United States Patent [19]

Johansson et al.

[11] 4,352,790

[45] Oct. 5, 1982

[54] MEDICAL PREPARATION CONTAINING PROSTAGLANDIN

[75] Inventors: Olof J. A. Johansson, Veberöd; Ulf I. Ulmsten, Malmö, both of Sweden

[73] Assignee: Perstorp AB, Perstorp, Sweden

[21] Appl. No.: 112,563

[22] Filed: Jan. 16, 1980

[30] Foreign Application Priority Data

Jan. 29, 1979 [SE] Sweden ............................... 7900737

[51] Int. Cl.³ .................. A61K 31/74; A61K 31/215; A61K 31/19
[52] U.S. Cl. ...................................... 424/78; 424/305; 424/317
[58] Field of Search ..................... 424/305, 317, 78, 80

[56] References Cited

U.S. PATENT DOCUMENTS

| | | | |
|---|---|---|---|
| 3,888,975 | 6/1975 | Ramwell | 424/15 |
| 3,948,254 | 4/1976 | Zaffaroni | 128/127 |

FOREIGN PATENT DOCUMENTS

| | | |
|---|---|---|
| 7737420 | 12/1977 | France . |
| 1446626 | 8/1976 | United Kingdom . |
| 1465376 | 2/1977 | United Kingdom . |
| 1489779 | 10/1977 | United Kingdom . |
| 1516348 | 7/1978 | United Kingdom . |
| 1554783 | 10/1979 | United Kingdom . |

OTHER PUBLICATIONS

Thomas et al., Chem. Abst., vol. 90 (1979), p. 50935n.
Kawada, Chem. Abst., vol. 92 (1980), p. 169,243s.
Shimizu et al., Chem. Abst., vol. 90 (1979), p. 109,952w.
Okazaki et al., Chem. Abst., vol. 90 (1979), p. 61,245p.

*Primary Examiner*—Sam Rosen
*Attorney, Agent, or Firm*—Stevens, Davis, Miller & Mosher

[57] ABSTRACT

A stable prostaglandin containing medical preparation in the form of substantially dry particles and intended for intravaginal and/or intracervical application. The preparation comprises prostaglandin absorbed and/or adsorbed in a crosslinked hydroxyl group containing polymer which is insoluble in water but has capability of swelling in water containing liquids to form a gel.

10 Claims, No Drawings

MEDICAL PREPARATION CONTAINING PROSTAGLANDIN

The present invention relates to a stable prostaglandin containing medical preparation in the form of substantially dry particles and intended for intravaginal and/or intracervical application.

Prostaglandins, which are a group of fatty acid derivatives with strong biological effects, have for example been used for about ten years within the medical field to expediate the completion or interruption of pregnancy at different kinds of pregnancy complications and also to cause legal abortion. The prostaglandins have been used in the form of a solution for intrauterine or intravenous administration and tablets for peroral administration. At intravenous administration as well as at peroral administration a high dosage is needed to obtain an adequate effect. However, this results in common side effects, such as indisposition, vomiting and diarrhoea for example.

With intrauterine administration similar side effects occur. In order to bring about an adequate effect the administration of the prostaglandin solution must then be carefully regulated and also prolonged for a long time.

One has also applied prostaglandin as a viscous solution in cervix uteri to expediate the ripening of the cervix, which facilitates an optional start of the delivery. A similar method has been used to facilitate and thereby reduce the risks of an interruption of the pregnancy to cause a legal abortion. Then for example hydroxypropylmethyl cellulose has been used as a viscosity increasing agent. The intention is then that the solution by the high viscosity will stay better on the treatment surface (cervix uteri). There it can release prostaglandin which can then provide a local effect.

However, the preparation of such viscous slimes is time consuming. Cellulose derivatives such as hydroxypropylmethyl cellulose are of high molecular weight and difficult to dissolve. Moreover, it is difficult and time consuming to bring about a homogeneous mixture of prostaglandin and the dissolved cellulose derivative. The long formulation time results in a decrease of the prostaglandin activity and a risk of bacterial growth of the formulation. In order to obtain an adequate treatment by means of the formulation, this must be used within a few hours. Furthermore, the slime produced slides easily on mucous membrane surfaces. Therefore, it is difficult to get the slime to stay on the intended treatment surface. Now it has surprisingly turned out that the above mentioned problems connected with previously used prostaglandin containing preparations can be solved according to the present invention.

Thus, according to the present invention provides a stable prostaglandin containing medical preparation in the form of substantially dry particles and intended for intravaginal and/or intracervical application. The preparation comprises prostaglandin absorbed and/or adsorbed in a crosslinked, hudroxyl group containing polymer, which is insoluble in water but has a capability of swelling in water-containing liquids to form a gel.

Preferably, the preparation is intended for facilitating the start of delivery and the interruption of pregnancy at a legal abortion respectively.

The preparation according to the invention is preferably containing prostaglandins from group E or F or derivatives thereof. Prostaglandin $E_2$ ($PGE_2$) and prostaglandin $F_{2\alpha}$ ($PGF_{2\alpha}$) are two very suitable prostaglandins. However, also other prostaglandins can be present in the preparation.

The water insoluble but swellable, crosslinked, hydroxyl group containing polymer of the preparation is either known before or can be produced analogously to such known polymers. For example, it can consist of a polymer polyalcohol such as polyvinyl alcohol; a polymer carbohydrate, for example starch, dextran, inulin or a derivative thereof, for instance hydroxypropyl starch or hydroxyethyl cellulose; a polymerized carbohydrate, for example dextrin, saccharose, maltose, sorbitol or a derivative thereof.

The above swellable polymers have been crosslinked in different ways. For instance, this can be brought about by reaction and/or polymerization with a bifunctional organic substance such as epichlorohydrin.

Such crosslinked polymers are known from the Swedish Pat. Nos. 169,293, 209,018 and 358,894 for example.

As examples of suitable bifunctional substances for carrying out the process may in the first place be mentioned bifunctional glycerine derivatives, such as epichlorohydrin, dichlorohydrin, epibromohydrin and dibromohydrin, further 1,2- 3,4-diepoxybutane, diepoxypropylether, diepoxypropylethers of ethyleneglycol, propyleneglycol, polyethylene glycols and similar compounds. Generally, aliphatic diepoxy compounds containing carbon, hydrogen, oxygen and without dissociable groups are suitable for the purpose.

The swellable polymer used according to the invention can contain anionic or cationic groups. Such groups can be chemically bonded to the polymer before or after the crosslinking according to the Swedish Pat. Nos. 204,906 and 222,291.

An important property of the preparation according to the invention is its swelling ability in water. The swelling ability can be expressed in ml/g and it can be measured by letting one gram of the preparation in the form of dry particles swell fully in a graduated measuring glass containing a surplus of water, whereupon the sedimented gel volume is read off. The preparation according to the invention can have a swelling ability of 1.5–100 ml/g, preferably 2–50 ml/g, for example between 4 and 20 ml/g.

According to the invention the prostaglandin will be absorbed and/or adsorbed in the hydrophilic, insoluble but swellable polymer as mentioned above. This can for instance be brought about by treating the dry or swelled polymer with a prostaglandin solution. If the swellable polymer is used in a dry state it is preferable to have a certain amount of water present so the polymer is swelling to a gel. Then the absorption of the prostaglandin into the swellable polymer is facilitated.

Thereafter the preparation is dried. Due to the temperature sensitivity of the prostaglandin freeze-drying is a suitable drying method.

The preparation according to the invention can be used in different application forms. Thus, it can be used as such in the form of substantially dry particles.

The preparation can also be used as a substance in a viscous suspension, for example suspended in a physiological sodium chloride solution or suspended in for example glycerine or macrogol.

The preparation can also be present as an active substance in other application forms, such as ointments or suppositories.

The different application forms can be radiation sterilized in connection with the production.

If the preparation is used in the form of dry particles or as a suspension it can suitably be applied intravaginally and/or intracervically by means of a syringe provided with a tube.

Quite surprisingly the new preparation has turned out to have much better qualities than previously known prostaglandin containing preparations. For example, the new preparation has a very good storage stability. Thus, it can be stored for at least a year without any risk of inactivation or contamination. The preparation can also be prepared quickly as a suspension for clinical use for example. The short preparation time gives a decreased risk of microbial contamination and growth. The viscosity of the suspension can easily be regulated by varying the amount of suspension medium. At the use of the preparation no adverse systemic or local reactions have been observed.

The invention will be explained further in connection with the embodiment examples below.

EXAMPLE 1

550 g dextrin were dissolved in 500 ml 2 N sodium hydroxide solution containing 3.5 g sodiumboron hydride. The solution thus obtained was introduced into another solution consisting of 800 ml toluene and 20 g stabilizer GAC PE 510 (sold by GAF Corporation, USA). The dextrin solution was emulgated in the toluene solution while stirring and heating to 70° C. 50 ml epichlorohydrin were added, whereupon the reaction was continued for 4 hours at 70° C. The reaction mixture was cooled, whereupon the toluene was separated. The reaction mixture was then washed with water, neutralized, washed with sterilized distilled water, treated with 95% ethanol and sucked dry.

The product was dried at 70° C. for 15 hours. Then 493 g of the product were obtained.

In turn 50 injection bottles a 10 ml were each provided with 0.7 g of the above product (particle size 50–100 um), 25 microliters distilled sterilized water and 50 microliters prostaglandin solution containing 1% (weight/volume) prostaglandin $E_2$ in ethanol, (Dinoprostone ®, Upjohn Ltd, Crawley, Sussex, England).

After the additions, the injection bottles were shaken to homogenize the product, whereupon it was freeze-dried.

The preparation in one injection bottle is enough for one treatment. The preparation had a swelling ability of 6.3 ml/g.

The preparation was used in different application forms. Thus, it was used (1) as dry particles, (2) as a suspension in 5 ml sterile physiological sodium chloride solution and (3) as a suspension in 0.35 g Unguentum Macrogoli and 0.35 g Macrogolum 400.

The preparations were homogenized before the application.

EXAMPLE 2

100 g sorbitol (Merck, Sorbit Griessform DAB 7) were dissolved in 80 g 50 percent by weight sodium hydroxide solution. The solution thus obtained was introduced into another solution consisting of 150 ml toluene containing 4.5 g stabilizer GAC PE 510. The sorbitol solution was emulgated in the toluene solution while stirring and heating to 70° C. 55 ml epichlorohydrin were added, whereupon the reaction was continued for 4 hours at 70° C. The reaction mixture was cooled, whereupon the toluene was separated. The reaction mixture was washed with water, neutralized, washed with sterilized distilled water, treated with 95% ethanol and sucked dry.

The product was dried at 70° C. for 15 hours. Then 39 g of the product were obtained.

In turn 10 injection bottles a 10 ml were each provided with 0.5 g of the above product (particle size 50–100 um) and 60 microliters prostaglandin solution containing 0.50 mg prostaglandin $E_2$ (same product as in Example 1) in an aqueous solution containing 83 percent by weight ethanol.

After the additions the injection bottles were shaken to homogenize the product, whereupon it was freeze-dried.

The preparation in one injection bottle is enough for one treatment.

The preparation had a swelling ability of 10.6 ml/g.

The preparation was used in the form of dry particles.

EXAMPLE 3

In turn 10 injection bottles a 10 ml were each provided with 0.5 g dextran based product, Sephadex ® G-50 (particle size 50–150 um, Pharmacia Fine Chemicals, Uppsala, Sweden) and 60 microliters prostaglandin solution containing 0.50 mg prostaglandin $E_2$ (same product as in Example 1) in an aqueous solution containing 83 percent by weight ethanol.

After the additions, the injection bottles were shaken to homogenize the product, whereupon it was freeze-dried.

The preparation in one injection bottle is enough for one treatment.

The preparation had a swelling ability of 9.4 ml/g.

The preparation was used in the form of dry particles.

EXAMPLE 4

25 g hydroxyethyl cellulose were dissolved in 500 ml 0.8 N sodium hydroxide solution containing 2 g sodiumboron hydride. The solution thus obtained was introduced into another solution consisting of 500 ml toluene containing 20 g stabilizer GAC PE 510 (sold by GAF Corporation, USA). The hydroxyethyl cellulose solution was emulgated in the toluene solution while stirring and heating to 70° C. 5 ml epichlorohydrin were added, whereupon the reaction was continued for 4 hours at 70° C. The reaction mixture was cooled, whereupon the toluene was separated. The reaction mixture was then washed with water, neutralized, washed with sterilized distilled water, treated with 95% ethanol and sucked dry.

The product was dried at 70° C. for 15 hours. Then 17 g of the product were obtained.

In turn 10 injection bottles a 10 ml were each provided with 0.3 g of the above product and 100 microliters prostaglandin solution containing 0.83 mg prostaglandin $E_2$ (Dinoprostone ®, Upjohn Ltd, Crawley, Sussex, England) in an aqueous solution containing 83 percent by weight ethanol.

After the additions, the injection bottles were shaken to homogenize the product, whereupon it was freeze-dried.

The preparation in one bottle is enough for one treatment. The preparation had a swelling ability of 92 ml/g.

The preparation was used in the form of dry particles.

EXAMPLE 5

The long term stability of the preparation according to the invention was tested in the following way.

A number of injection bottles containing a freeze-dried preparation produced according to Example 1 were stored at room temperature. Each bottle contained 0.5 mg prostaglandin $E_2$ ($PGE_2$). The $PGE_2$ content of these bottles was tested after 4, 6, 8, 18 and 52 weeks and found to be 97.2, 97.8, 96.1, 95.5 and 92.5 percent respectively of the original content.

The manufacturer (The Upjohn Company) of the prostaglandin $E_2$ of the preparations produced according to the above Examples 1–4 has previously shown (see Journal of Pharmaceutical Sciences Vol. 68 No. 1, pages 114–115, January 1979) that the stability of the prostaglandin $E_2$ is rapidly decreasing after a storage of about 6 months at 25° C. Thus, after 12 months only about 65% of the original content of prostaglandin $E_2$ is remaining.

Consequently, the preparation according to the invention has got a far better storage stability than the pure compound ($PGE_2$).

EXAMPLE 6

10 injection bottles were each provided with 0.7 g of the preparation produced according to Example 1 and containing 0.25 mg prostaglandin $E_2$. 2.6 ml physiological sodium chloride solution were added to each of the bottles. The preparation then swelled to a viscous suspension within 30 seconds. An easily-handled suspension (gel) ready for direct use was obtained.

Ten women were treated with a single dose of the above suspension by intracervical application. Before the application of the preparation the cervical dilatation was registered by Hegar dilators. The cervix consistency was estimated according to a simple scale, 1=hard, 2=moderately soft and 3=soft. The women were supervised in the hospital over the night and they were instructed to list possible side effects of the preparation. Next morning, i.e. approximately 12 hours after the application of the preparation, the cervical state was re-evaluated.

The abortion was performed by dilatation and evacuation. The patients were leaving the hospital approximately 6 hours after the surgical procedure. The patients were checked after one and four weeks. The result of the cervical ripening is shown in the table and the description below.

|  | Before the treatment | After the treatment |
| --- | --- | --- |
| Cervical dilation | 4.4 mm | 9.1 mm |
| Cervical consistency | 1.3 | 2.3 |

By the treatment a rapid cervical ripening was obtained which facilitated the subsequent abortion. No adverse systemic or local reactions were found during or after the treatment with the preparation according to the invention.

The invention is not limited to the embodiments shown, since these can be modified in different ways within the scope of the present invention.

I claim:

1. A stable medical preparation containing prostaglandin in the form of substantially dry particles and intended for intravaginal or intracervical application, said preparation comprising a crosslinked hydroxyl group containing polymer which is insoluble in water but has the capability of swelling in liquid containing water to form a gel, said polymer containing an effective amount of prostaglandin.

2. A preparation according to claim 1, wherein the polymer consists of a crosslinked polymer carbohydrate or a crosslinked polymerized carbohydrate.

3. A preparation according to claim 1, wherein the crosslinking of the polymer has been brought about by reaction with epichlorohydrin.

4. A preparation according to claim 1, wherein the dry particles have such a swelling capability that 1 gram of these particles forms a gel with a volume of 1.5–100 ml at a complete swelling in water.

5. A preparation according to claim 4, wherein the dry particles have such a swelling capability that 1 gram of these particles forms a gel with a volume of 2–50 ml at a complete swelling in water.

6. A preparation according to claim 1, which comprises prostaglandin from group E or F or derivatives thereof.

7. A preparation according to claim 6, which comprises at least one of the compounds prostaglandin $E_2$ or prostaglandin $F_{2\alpha}$.

8. A preparation according to claim 2, wherein the crosslinked carbohydrate polymer and the crosslinked polymerized carbohydrate are selected from the group consisting of crosslinked starch, dextran, inulin, cellulose, dextrin, saccharose, maltose, sorbitol polymer or an operable derivative thereof.

9. A method of expediting the ripening of the cervix uteri, which comprises administering intracervically or intravaginally to a patient an effective amount of a crosslinked hydroxyl group containing polymer which is insoluble in water but swells in liquid containing water to form a gel, said polymer containing an effective amount of prostaglandin.

10. The method of claim 9, wherein the polymer is administered as (1) dry particles, (2) in a viscous suspension, (3) in an ointment or (4) in a suppository.

* * * * *